(12) United States Patent
Boyer et al.

(10) Patent No.: US 9,851,440 B1
(45) Date of Patent: Dec. 26, 2017

(54) SUBSURFACE IMAGING SYSTEM AND METHOD FOR INSPECTING THE CONDITION OF A STRUCTURE

(71) Applicant: STATE FARM MUTUAL AUTOMOBILE INSURANCE COMPANY, Bloomington, IL (US)

(72) Inventors: Patrick H. Boyer, Bloomington, IL (US); Nathan L. Tofte, Downs, IL (US); Jackie O. Jordan, II, Bloomington, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 0 days.

(21) Appl. No.: 15/170,430

(22) Filed: Jun. 1, 2016

Related U.S. Application Data

(63) Continuation of application No. 14/810,188, filed on Jul. 27, 2015, now Pat. No. 9,389,314.

(51) Int. Cl.
*G01S 13/89* (2006.01)
*G01S 15/89* (2006.01)
*G01S 7/41* (2006.01)
*G01S 7/539* (2006.01)

(52) U.S. Cl.
CPC ............... *G01S 13/89* (2013.01); *G01S 7/411* (2013.01); *G01S 7/539* (2013.01); *G01S 15/89* (2013.01)

(58) Field of Classification Search
CPC .......... G01S 15/89; G01S 15/10; G01S 7/523; G01S 7/28; G01S 13/89; G01S 13/10; G01B 17/02; G01B 7/06
USPC .................. 73/597, 598, 599, 600, 602, 627
See application file for complete search history.

(56) References Cited

U.S. PATENT DOCUMENTS

| 8,833,168 | B2 * | 9/2014 | Kitazawa | G01N 29/069 73/602 |
| 8,872,818 | B2 | 10/2014 | Freeman et al. | |
| 2008/0006087 | A1 * | 1/2008 | Winter | G01B 17/02 73/584 |
| 2008/0245150 | A1 | 10/2008 | Katayama et al. | |
| 2009/0265193 | A1 | 10/2009 | Collins et al. | |
| 2013/0087399 | A1 | 4/2013 | Slawinski et al. | |

* cited by examiner

*Primary Examiner* — Laura Martin
*Assistant Examiner* — Rose M Miller
(74) *Attorney, Agent, or Firm* — Marshall, Gerstein & Borun LLP; Randall G. Rueth

(57) ABSTRACT

In a method and system for inspecting the condition of a structure, the structure is scanned with a three-dimensional (3D) scanner. The 3D scanner includes a sensing system having one of a radar sensing device or an ultrasonic detection device. The sensing system detects 3D information about a subsurface of the structure, and the 3D scanner generates 3D data points based on the information detected by one or more of the radar sensing device and the ultrasonic detection device. A 3D model is constructed from the 3D data and is then analyzed to determine the condition of the subsurface of the structure.

16 Claims, 11 Drawing Sheets

SUBSURFACE IMAGING SYSTEM AND METHOD FOR INSPECTING THE CONDITION OF A STRUCTURE

CROSS-REFERENCE TO RELATED APPLICATION

The present application is a continuation of U.S. application Ser. No. 14/810,188, filed Jul. 27, 2015, entitled "Subsurface Imaging System and Method for Inspecting the Condition of a Structure," which is hereby incorporated by reference for all purposes.

TECHNICAL FIELD

This disclosure relates to property inspection methods and systems, and in particular, to property inspection systems and methods for inspecting the condition of a structure using a subsurface imaging system and method.

BACKGROUND

After an accident or loss, property owners typically file claims with their insurance companies. In response to these claims, insurance agents or representatives investigate the claims to determine the extent of damage and/or loss, ultimately providing their clients with appropriate compensation.

Determining and documenting the extent of damage can be risky for the appraiser. For example, in a situation where a structure has experienced roof damage, appraisers typically climb onto the roof to evaluate the damage. When climbing onto the roof and maneuvering around the roof for the inspection, the appraiser runs a risk of injury, especially in difficult weather conditions, where the roof may be slippery because of rain, snow, and/or ice and winds may be severe.

Even if the appraiser is not injured, the inspection process is time consuming and inefficient. Once on the roof, appraisers may take a digital picture of the damaged area. Afterwards, the picture is typically attached to an electronic claim file where it can later be analyzed by an appraiser to estimate the extent of damage to the structure. Two-dimensional digital pictures or video of a roof or structure often provide inadequate detail for a thorough inspection of a structure. Issues like poor image quality resulting from camera movement, bad lighting or out-of-focus images can make it difficult to estimate the condition of a property based on an image. To address some of these issues, insurance companies may use 3D-scanners to get a more detailed view of the surface of the roof.

However, both two-dimensional images (2D) and many three-dimensional (3D) surface scans, for example, are unable to capture damage that may have occurred beneath the surface of a roof (e.g., damage to lower layers of shingles, moisture accumulation, rotting of lower layers). For example, a fiberglass mesh layer of a roof that is disposed beneath the surface of the roof may be damaged by impacts and cause a visible divot. Heat from the sun on the roof, however, often causes such divots to reset, making it appear as though the fiberglass mesh layer was not damaged. As a result, such damage to subsurface structures often goes undetected during 2D and 3D surface scans, interfering with, if not preventing, accurate estimates and appraisals of the condition of a structure and/or damage to the structure.

SUMMARY

A system and method of inspecting the condition of a structure is disclosed. In one example, the method of inspecting a structure includes deploying one or more three-dimensional (3D) scanners to scan a structure, wherein the one or more 3D scanners are communicatively coupled to a memory; and detecting 3D information about a subsurface of the structure by implementing a sensing device including one or more of a radar sensing device or an ultrasonic detection device coupled to the one or more 3D scanners. Implementing the sensing device includes: transmitting, via at least one transmitter, pulses to at least one point of a plurality of points of the subsurface of the structure; receiving, via at least one receiver, one or more reflected signals from at least one point of a plurality of points of the subsurface of the structure; and determining, via one or more processors, a distance from one of the radar sensing device or the ultrasonic detection device to at least one point of the plurality of points of the subsurface of the structure based on the at least one received reflected signal. The method further comprises generating, at the one or more 3D scanners, a plurality of 3D data points, wherein at least one point of the plurality of 3D data points correspond to at least one point of a plurality of points in the subsurface of the structure detected by the radar sensor device or the ultrasonic detection device during the scan of the structure. The method still further comprises causing one or more processors communicatively coupled to the memory to generate an estimation of the condition of the subsurface of the structure based on the plurality of 3D data points.

In another example of the present disclosure, a property inspection system for inspecting the condition of a structure comprises one or more three-dimensional (3D) scanners adapted to scan a surface of the structure and a sensing device including one or more of a radar sensing device or an ultrasonic detection device coupled to the one or more 3D scanners. Each of the radar sensing device and the ultrasonic detection device has at least one transmitter, at least one receiver, and at least one processor. In addition, each sensing device is adapted to detect 3D information about a subsurface of the structure by: (1) transmitting, via the at least one transmitter, pulses to at least one point of a plurality of points of the subsurface of the structure; (2) receiving, via at least one receiver, one or more reflected pulses from at least one point of a plurality of points of the subsurface of the structure; and (3) determining, via at least one processor, a distance from one or more devices to at least one point of the plurality of points of the subsurface of the structure based on the at least one received reflected pulse. Further, the system comprises at least one processor adapted to generate 3D data points corresponding to the 3D information detected by one or more of the radar sensing device or the ultrasonic sensing device, and a memory, communicably coupled to the one or more 3D scanners, adapted to store 3D data points generated by the one or more processors and the 3D information detected by the radar sensing device or the ultrasonic detection device. Still further, the system comprises a network interface, communicably coupled to the one or more processors, adapted to transmit the 3D data points to a data analysis system for estimating the condition of the subsurface of the structure.

BRIEF DESCRIPTION OF THE DRAWINGS

The Figures described below depict various aspects of the system and methods disclosed therein. It should be understood that each figure depicts an example of a particular aspect of the disclosed system and methods, and that each of the figures is intended to accord with a possible example thereof. Further, wherever possible, the following description refers to the reference numerals included in the following figures, in which features depicted in multiple figures are designated with consistent reference numerals.

There are shown in the drawings arrangements which are presently discussed, it being understood, however, that the present examples are not limited to the precise arrangements and instrumentalities shown, wherein.

DETAILED DESCRIPTION

Generally, a system and method for inspecting the condition of a physical structure is disclosed. The system includes one or more three-dimensional (3D) scanners adapted to scan a surface of the structure and a sensing device comprising one or more of a radar sensing device or an ultrasonic detection device coupled to the one or more 3D scanners. Each of the radar sensing device and the ultrasonic detection device comprises at least one transmitter, at least one receiver, and at least one processor. In addition, each sensing device is adapted to detect 3D information about a subsurface of the structure by: (1) transmitting, via the at least one transmitter, pulses to at least one point of a plurality of points of the subsurface of the structure; (2) receiving, via at least one receiver, one or more reflected pulses from at least one point of a plurality of points of the subsurface of the structure; and (3) determining, via at least one processor, a distance from one or more of the devices to at least one point of the plurality of points of the subsurface of the structure based on the at least one received reflected pulse. The system further includes at least one processor adapted to generate 3D data points corresponding to the 3D information detected by the radar sensing device or the ultrasonic sensing device. A memory, communicably coupled to the one or more 3D scanners, is adapted to store 3D data points generated by the one or more processors and the 3D information detected by the radar sensing device or the ultrasonic detection device.

Figure 1:
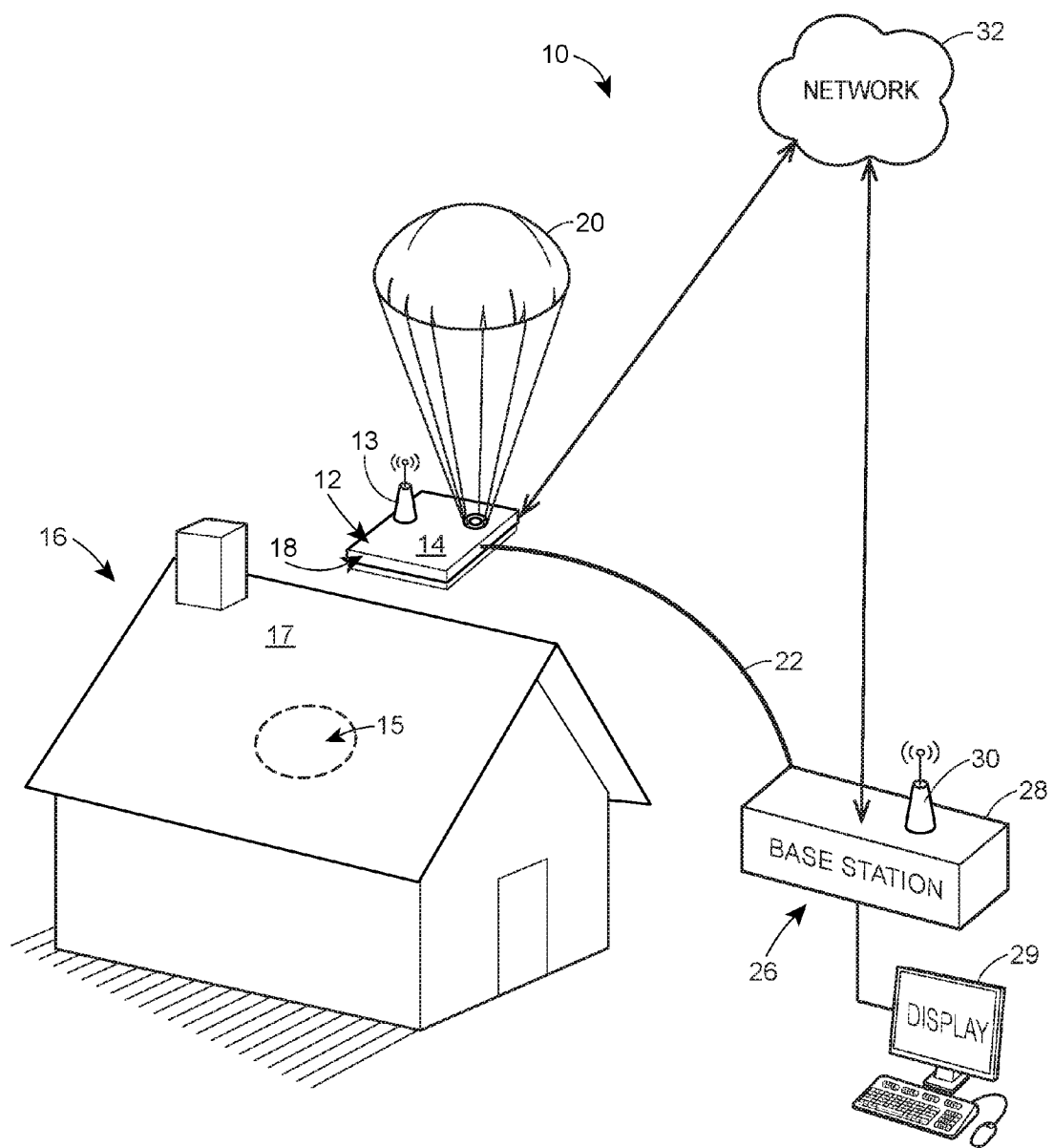
FIG. 1 is a perspective view of a property inspection system according to one example of the present disclosure.

More specifically, and referring now to FIG. 1, a property inspection system 10 of the present disclosure is depicted. The property inspection system 10 includes at least one 3D scanner 12 having a base 14, an antenna 13, and at least one sensing system 18 coupled to the base 14 of the 3D scanner 12. The sensing system 18 may include an ultrasonic detection device or a radar sensing device. The 3D scanner 12 may be disposed above a structure 16, in particular a fixed distance, such as three feet, above a plurality of points 15 of a surface 17 of the structure 16, such as a roof, to inspect the condition of the structure 16, for example. In another example, as explained in more detail below, the 3D scanner is disposed on the surface 17 of the structure to inspect the condition of the structure 16.

As further depicted in FIG. 1, the 3D contact scanner 12 may be affixed to a flying device 20, such as a balloon, which may be used to position the 3D scanner 12 onto or just above the surface 17 of the structure 16, e.g., the roof of the structure 16. While the flying device 20 depicted in FIG. 1 is a balloon, the flying device 20 may alternatively be an airplane, a helicopter, a projectile, a rocket, or any other device capable of flight, levitation or gliding. In yet another example, the 3D scanner 12 may also be affixed to a remotely controlled device, such as a radio controlled device; a device that rolls, drives, crawls or climbs; a mechanical apparatus affixed to or near the structure; or a satellite. In addition, the 3D scanner 12 may be held and operated by a person (not shown).

As also depicted in FIG. 1, the 3D scanner may be tethered via a tether line 22 to a base station 28 of a data analysis system 26. In some examples, the tether 22 may provide power to the flying device 20. The tether 22 may also provide a communication channel between the flying device 20 and the base station 22 (and may replace antennas in certain examples).

The property inspection system 10 may further include a data analysis system 26. The data analysis system 26 may include a base station 28, display 29, and an antenna 30, which may be in communication with the antenna 13 of the 3D scanner 12, as explained more below. Alternatively, the data analysis system 26 of the property inspection system 10 may be in communication with the 3D scanner 12 via a network 32, such as a wireless network. As one of ordinary skill in the art will appreciate, the network 32 may be a single network, or may include multiple networks of one or more types (e.g., a public switched telephone network (PSTN), a cellular telephone network, a wireless local area network (WLAN), the Internet, etc.). In some examples, the network 32 may include one or more devices such as computers, servers, routers, modems, switches, hubs, or any other networking equipment.

In addition, while the structure 16 depicted in FIG. 1 is a building, which may be residential, commercial, industrial, agricultural, educational, or of any other nature, the structure 16 may be any type of construction or object and still fall within the scope of the present disclosure. For example, the structure 16 may alternatively be personal property, such as a vehicle, boat, aircraft, or furniture.

The property inspection system 10 may be utilized in a number of situations, but in the preferred example, a user associated with an insurance company utilizes the property inspection system 10 for the purpose of inspecting the condition of the subsurface of the structure. In another example, the property inspection system 10 is additionally used for the purpose of estimating the condition of a subsurface of the structure 16 based on the information detected about the subsurface of the structure during the inspection. For example, an insurance policy-holder may file a claim because the policy-holder believes that the structure 16 is damaged. A user (e.g., an insurance company or claim adjuster) may then deploy the property inspection system 10 to inspect the structure 16 and estimate the condition of the structure 16. For example, the property inspection system 10 may determine that the roof of the structure 16 is damaged and then calculate how much it will cost to fix the roof.

Figure 2:
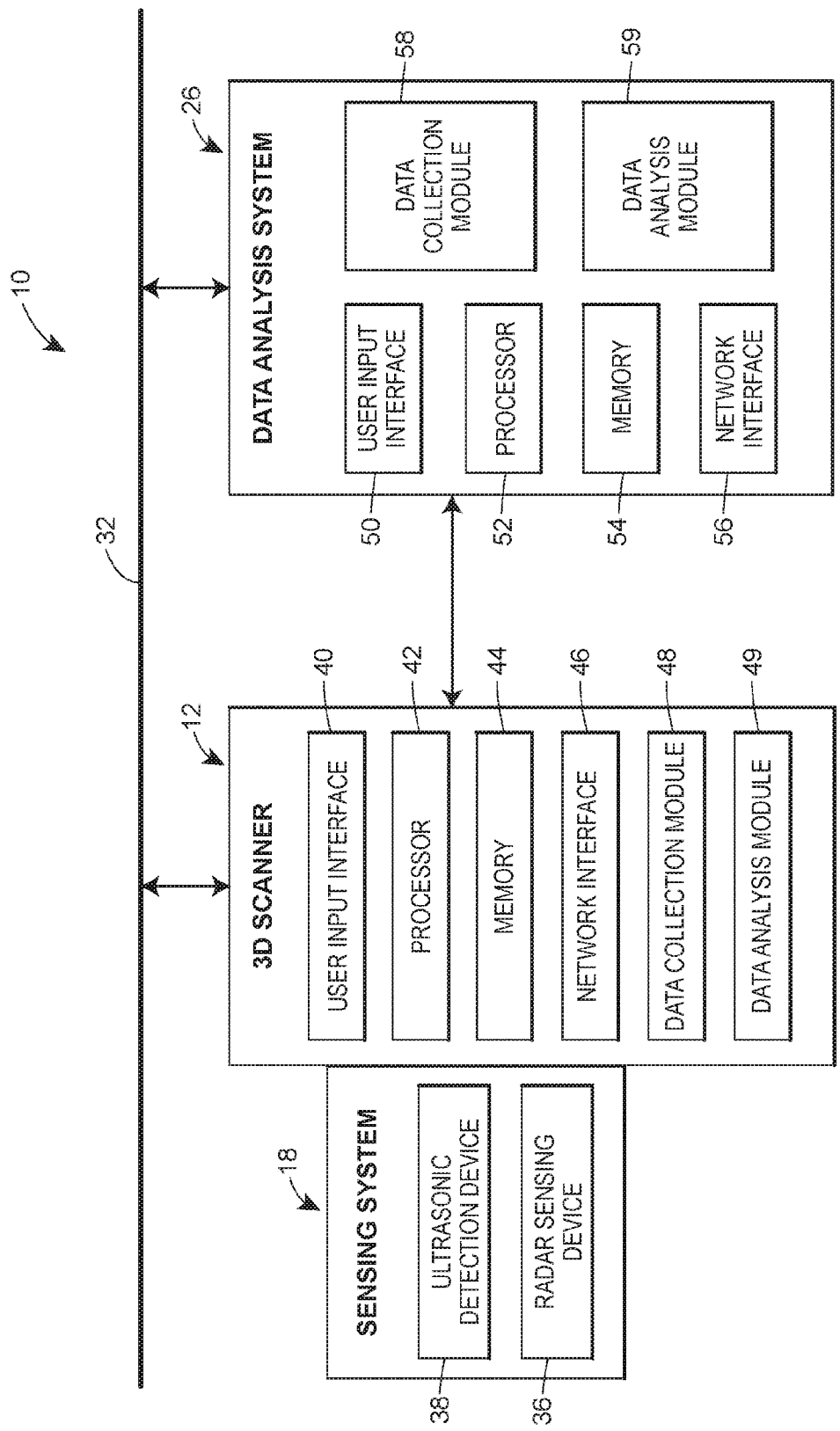
FIG. 2 is a block diagram of the property inspection system of FIG. 1.

Referring now to FIG. 2, a block diagram of the property inspection system 10 of FIG. 1 is depicted. More specifically, the property inspection system 10 includes the 3D scanner 12 that is communicably coupled to the data analysis system 26 via the network 32. Alternatively, and as noted, the 3D scanner 12 may be coupled to the data analysis system 26 via a direct wired connection. The 3D scanner 12 is communicably coupled to the sensing system 18 that includes one or more of a radar sensing device 36 and an ultrasonic detection device 38, each of which is coupled to the 3D scanner 12. More specifically, the radar sensing device 36 and the ultrasonic detection device 38 may be a part of the 3D scanner 12 or a stand-alone device that is communicably coupled to the 3D scanner 12.

As further depicted in FIG. 2, in one example, the 3D scanner 12 further includes a user input interface 40, at least one processor 42, a memory coupled to the processor 44, a network interface 46, a data collection module 48, and a data analysis module 49. In a similar manner, the data analysis system 26 also includes a user input interface 50, a processor 52, a memory 54, network interface 56, a data collection module 58 and a data analysis module 59.

In certain examples, the memory 44 of the 3D scanner 12 and the memory 54 of the data analysis system 26 may include volatile and/or non-volatile memory and may be removable or non-removable memory. For example, the memory 44, 54 may include computer storage media in the form of random access memory (RAM), read only memory (ROM), EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information. In addition, the network interface 46, 56 may include an antenna, a port for wired connection, or both.

In one example operation of the property inspection system 10, the data collection module 48 of the 3D scanner 12 generates data representing information detected by one or more of the radar sensing device 36 or the ultrasonic detection device 38. The data collection module 48 may then transmit the generated data over the network 32 to the data analysis module 59 of the data analysis system 26. The data analysis module 59 may then estimate a condition of the structure by analyzing the generated data. Alternatively, the data collection module 48 may transmit the generated data to the data analysis system 49 of the 3D scanner 12, and the data analysis system 49 may then estimate the condition of the structure 16 by analyzing the generated data.

In some examples, estimating the condition of the structure may include comparing the generated data to reference data stored in one or more of the memory 44 of the 3D scanner 12 or the memory 54 of the data analysis system 26. The reference data may be any type of data that can provide a point of comparison for estimating the condition of the structure 16. For example, the reference data of the memory 44, 54 may represent and/or include an image, a model, or any previously collected or generated data relating to the same or a similar structure or images or model unrelated to the scanned structure. Further, either data analysis module 49, 59 may use the estimate of the condition of the structure 16 to determine that the structure 16 is damaged, and then may calculate an estimated cost based on the extent of the damage to the structure 16.

More specifically, and in one example operation of the 3D scanner 12, the network interface 46 of the 3D scanner 12 may receive data, such as a signal representing a command to collect information about the structure 16. The network interface 46 then transmits the command to the processor 42 of the 3D scanner 12. The processor 42 then transmits a signal instructing the 3D scanner 12 to detect 3D characteristics associated with an object, a surface or a subsurface of the structure 16. The 3D scanner 12, along with one or more of the radar sensing device 36 or the ultrasonic detection device 38, detects the subsurface of the structure 16 and generates data representing 3D characteristics about the subsurface and/or surface of the structure 16 corresponding to the collected 3D information.

Figures 3A, 3B:
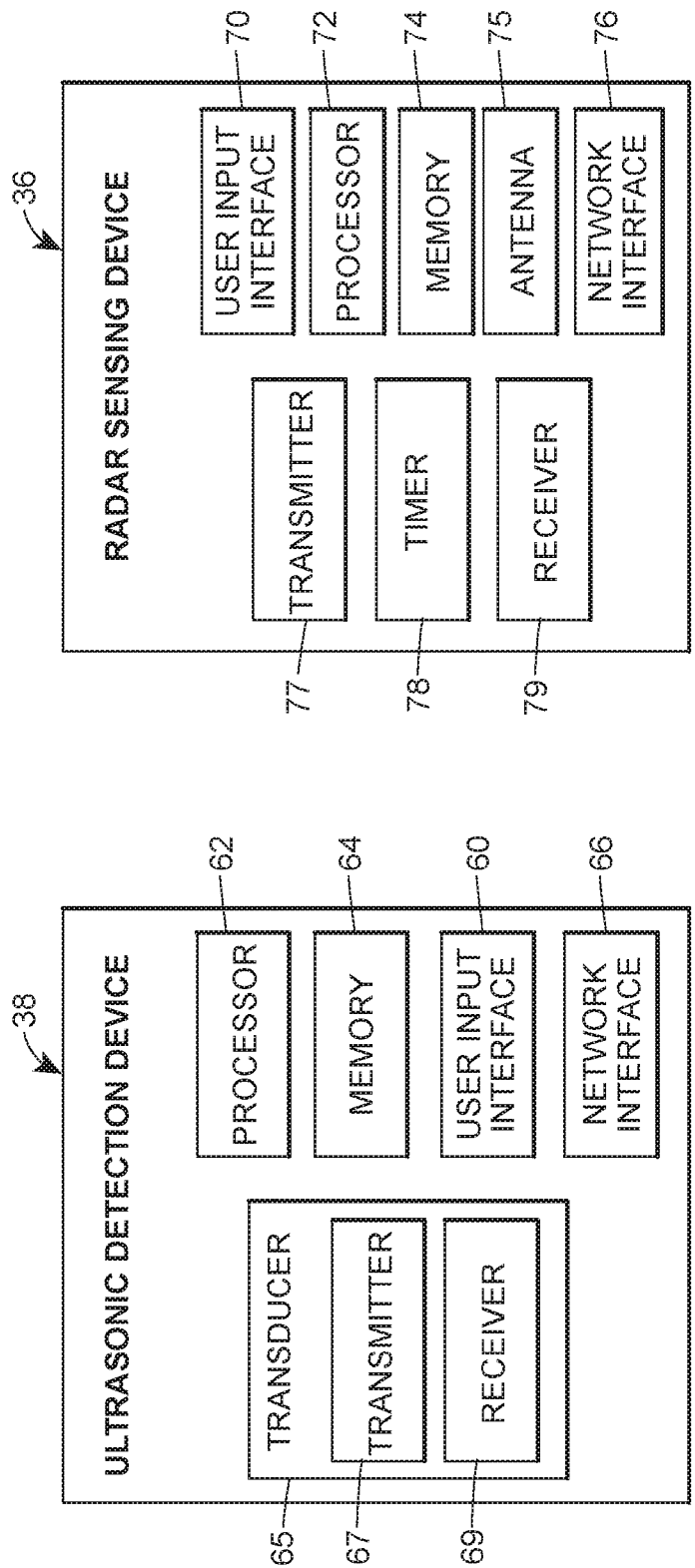
FIG. 3A is a block diagram of an ultrasonic detection device of FIG. 2.
FIG. 3B is a block diagram of a radar sensing device of FIG. 2.

Referring now to FIG. 3A, a block diagram of the ultrasonic detection device 38 of the sensing system 18 of FIG. 2 is depicted. As depicted in FIG. 3A, the ultrasonic detection device 38 includes a user input interface 60, a processor 62, a transducer 65, and a network interface 66. The transducer 65 includes a transmitter 67 for sending or transmitting pulses, such as sound waves, and a receiver 69 for receiving the pulses, such as the sound waves. More specifically, high frequency, e.g., 1 to 5 megahertz, sound pulses, such as sound waves, are transmitted onto the surface 17 of the structure 16 and into a subsurface 19 (FIG. 4B) of the structure 16 to inspect the condition of the structure 16.

In one example, the transducer 65 includes a probe having the transmitter 67 and the receiver 69. The transducer 65 may take the form of various shapes and sizes, and the shape of the transducer probe, for example, determines its field of view. The frequency of emitted pulses, such as sound waves, determines how deep the sound waves penetrate a structure or object and the resolution of an image ultimately generated from the same. The transducer 65 makes the sound waves and receives the reflected sound waves, also referred to as echoes, through the receiver 69, for example. Typically, the transducer 65 generates and receives sound waves using a principle called the piezoelectric (pressure electricity) effect, as one of ordinary skill in the art will understand.

More generally, a command to operate the ultrasonic detection device 38 at a desired frequency may be inputted into the network interface 66 of the ultrasonic detection device 38. The processor 62 will receive the command and instruct the transducer 65 to generate sound waves at the desired frequency. The reflected sound waves received by the receiver 69 of the transducer 65 may be stored in the memory 64 of the ultrasonic detection device 38 and accessed at a later time. Alternatively, the reflected sound waves received by the receiver 69 may be transmitted to the processor 62 that calculates the distance from the transducer 65 to a layer of the subsurface 19 of the structure 16 using the speed of sound in the structure and a time of each reflected sound wave's return, e.g., usually in the order of millionths of a second. Such calculations may then be saved to the memory 64 or transmitted over the network interface 66 of the ultrasonic detection device 38 to the data analysis system 26 (FIG. 1) and displayed on the display 29, in one example, and as explained in more detail below.

Referring now to FIG. 3B, a block diagram of the radar sensing device 36 of the sensing system 18 of FIG. 2 is depicted. Like the ultrasonic detection device 38, the radar sensing device 36 also includes a user input interface 70, a processor 72, a memory 74, a radar antenna 75, a network interface 76, a transmitter 77, a timer 78, and a receiver 79. The radar sensing device 36 uses a pulse or wave that may be transmitted from the transmitter 77, such as the radar antenna 75 to probe the subsurface 19 (FIG. 1) of the structure 16. The transmitted pulses or waves may be a high-frequency, e.g., 40 to 1500 MHz, electromagnetic pulse or wave or may also be a sound pulse or wave. The transmitted pulses or waves are reflected from various interfaces and layers in the subsurface 19, such that reflected waves are detected and received by the receiver 79. Reflecting interfaces may include water, a human-made object disposed in the subsurface of the structure, and/or a layer of the roof, as explained in more detail below, or any other surface having different properties. In one example, the received waves, such as returned waves or echoes, are processed by the processor 72, sent to the data analysis system 26 through the network interface 76, and displayed on the display 29 (FIG. 1) of the data analysis system 26. In another example, the received waves may be processed by the processor 72 and stored in the memory 74 to be accessed at a later time to evaluate the condition of the structure 16.

Figure 4A:
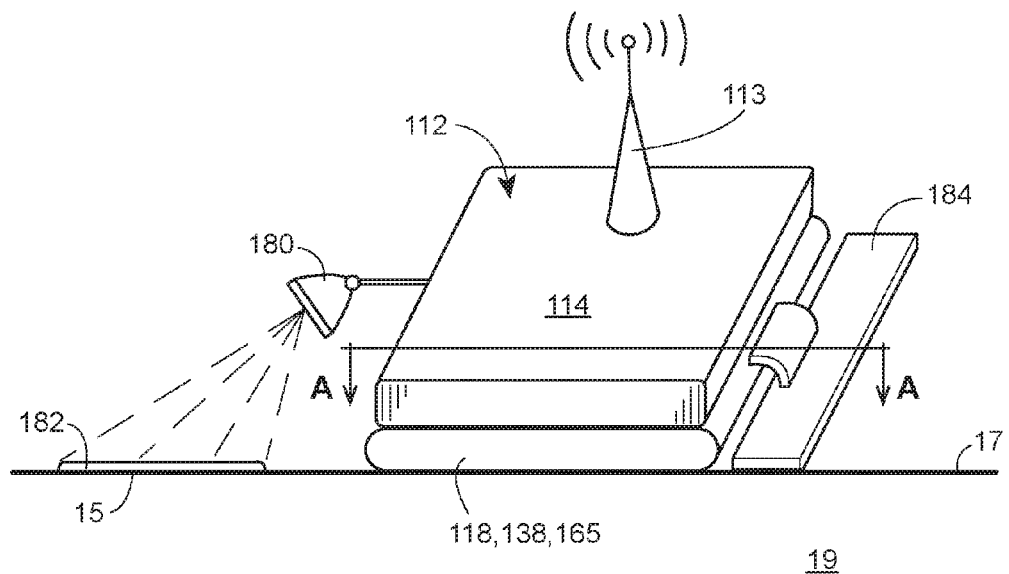
FIG. 4A is a perspective view of a 3D scanner and an ultrasonic detection device according to one aspect of the present disclosure.

Referring now to FIG. 4A, a 3D scanner 112 having an ultrasonic detection device 138 coupled thereto is depicted in contact with a top surface 17 of the structure 16 (FIG. 1). The 3D scanner includes a base 114, an antenna 113, a sensing system 118, the ultrasonic detection device 138, at least one transducer 165 and a spraying mechanism 180 coupled to a front portion of the base 114 of the 3D scanner 112. The spraying mechanism 180 operates to apply a sound conducting material 182, such as a jelly-like sound conducting material, to a plurality of points 15 on the surface 17 of the structure 16 before or during the scan by the 3D scanner 112. The at least one transducer 165 may be adapted to contact the sound conducting material 182 to detect 3D information about the subsurface 19. For example, the sound conducting material 182 may be used to improve the transmission of the sound waves from the at least one transducer 165 to the subsurface 19. The 3D scanner 112 also includes a suction device 184 that is coupled to a back portion of the base 114. The suction device 184 operates to collect the sound conducting material 182 from a plurality of points on the surface 17 after or during the scan by the 3D scanner 112. As one of ordinary skill in the art will appreciate, the suction device 184 may include a vacuum having a motor (not shown) and alternatively be coupled to a side portion of the base 114 without departing from the scope of the disclosure. In addition, while the suction device 184 depicted in FIG. 4A is rectangular in shape, the suction device 184 may alternatively include any other shape or combination of shapes, such as a square, a sphere, and a triangle, and also still fall within the scope of the present disclosure.

In one example operation, as the 3D scanner 112 moves across the top surface 17 of the structure 16 to affect a scan, the spraying mechanism 180 may first apply the sound conducting material 182 to a plurality of points 15 on the surface 17. This may occur before or while the sensing system 118 moves in one direction, such as to the left of the 3D scanner 112 in the orientation of FIG. 4A, and arrives at the same area of the surface 17 to perform a scan. As the 3D scanner 112 leaves an area of the surface 17 after performing a scan, the suction device 184 may then pass over the sound conducting material 182 on the plurality of points 15 on the surface 17 to remove any remaining sound conducting material 182. The suction device 184 may also include a filtration device (not shown) that is adapted to remove debris, such as rocks, dirt and leaves that may be suspended in the sound conducting material 182 after the sound conducting material 182 is removed the surface 17 of the structure 16. The sound conducting material 182 may then be reused or recycled.

Figure 4B:
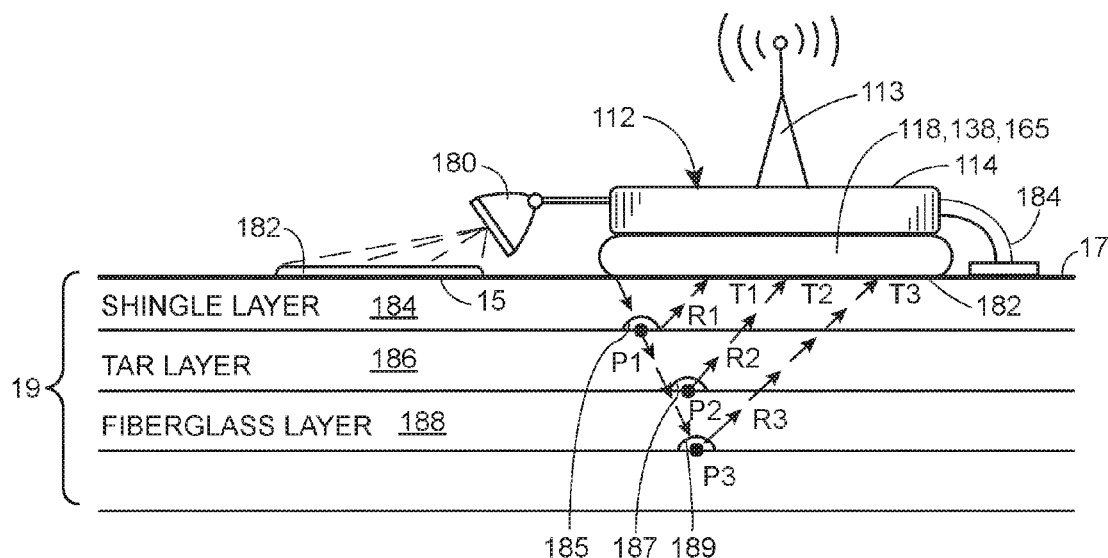
FIG. 4B is a cross-sectional view of the 3D scanner and the ultrasonic detection device of FIG. 4A, along with a subsurface of the structure, taken along the line A-A of FIG. 4A.

Referring now to FIG. 4B, a cross-section of subsurface 19 and a side view of the 3D scanner 112 along line A-A of FIG. 4A is depicted. The subsurface 19 may include a shingle layer 184, a tar layer 186 and a fiberglass layer 188, as well as other lower layers. Also depicted is a first plurality of points 185 disposed below the surface 17 of the structure or within the subsurface 19 of the structure 16. The first plurality of points 185 includes at least one point P1 and corresponds to a region between the shingle layer 184 and the tar layer 186. The subsurface 19 further includes a second plurality of points 187, which includes at least one point P2 and corresponds to a region between the tar layer 186 and the fiberglass layer 188. The subsurface 19 still further includes a third plurality of points 189, which includes at least one point P3 and corresponds to a region between the fiberglass layer 188 and lower layers.

As further depicted in FIG. 4B, the at least one transducer 65 (FIG. 4A) of the at least one ultrasonic detection device 138 is positioned on a portion of the sound conducting material 182, such that the at least one transducer 165 physically contacts the sound conducting material 182 in contact with the surface 17 of the structure 16. The at least one transducer 165 transmits at least one sound wave to the at least one point P1, P2, and/or P3 of the one or more of the first, second, and third plurality of points 185, 187, 189 of the subsurface 19 of the structure 16. The at least one transducer 165 then receives one or more reflected sound waves R1, R2, and/or R3 from at least one point P1, P2, and/or P3 of the one or more of the first, second, and/or third plurality of points 185, 187, 189 of the subsurface 19 of the structure 16.

As further depicted in FIG. 4B, the 3D scanner 112 may identify, via one or more processors 62 of the ultrasonic detection device 138, for example, a time T1, T2, and/or T3 corresponding to at least one of the reflected sound waves R1, R2 and/or R3 received by the transducer 165. More specifically, the times T1, T2, and T3 correspond to times from when the at least one sound wave is transmitted by the one or more transducers 165 to the at least one point P1, P2, P3 of the plurality of points 185, 187, 189 until the at least one reflected sound wave R1, R2, R3 is received by the at least one transducer 165. The received sound waves R1, R2, R3 may then be processed by the at least one processor 62 in the 3D scanner 112, such as the processor 42, and sent to the data analysis system 26 (FIG. 2). The data analysis system 26 may then identify, via one or more processors 52, at least one reflected sound wave R1, R2 and/or R3 that corresponds to the at least one layer 184, 186, 188 of the subsurface 19.

For example, the reflected wave R1 may correspond to a bottom of the shingle layer 184 and the reflected waves R2 and R3 may correspond to a bottom of the tar layer 186 and fiberglass layer 188, respectively. As one of ordinary skill in the art will appreciate, several reflected sound waves are possible from the same transmitted sound wave, depending on the frequency of the sound wave and the acoustic characteristics of the layers of the subsurface 19. Also, reflected waves used by the 3D scanner 112 may come either from the same transmitted sound wave or separate transmitted sound waves. These separate sound waves may be calibrated to go deeper into the subsurface 19, for example, by adjusting the frequency to allow the ultrasound pulse to travel deeper into the subsurface 19 and into layers lower than the fiberglass layer 188.

In one example, when effecting a scan, the transducer 165 of the 3D scanner 112 may transmit one or more ultrasonic sound waves and measure the time it takes for at least a portion of the transmitted sound wave to reflect off of at least one point of a plurality of points that correspond to at least part of one or more layers of the subsurface 19. The 3D scanner 112 may also generate a plurality of 3D points based on the received one or more reflected sound waves.

In addition, the 3D scanner 112 may calculate a number and thickness of the layers in subsurface 19. In one example, the number of layers may be calculated by causing one or more processors 42, 62 to add up the total number of reflected sound waves received that correspond to one or more separate layers 184, 186, 188 of the subsurface 19. In another example, one or more processors 42, 62 may calculate a thickness of one or more of the layers 184, 186, 188 by converting the time between reflected sound waves that corresponds to one or more separate layers 184, 186, 188 of the subsurface 19 into distances traveled by the reflected sound waves using the speed of the sound waves in the medium. This distance may correspond to the thickness of one or more layers 184, 186, 188 of the subsurface 19.

In one example, to calculate the thickness of the tar layer 186, the 3D scanner 112 may send the data corresponding to reflected sound waves R1, R2 and R3 to the data analysis system 26. The data analysis system 26 may then cause one or more processors 42, 62 to calculate a difference in arrival times T1 and T2, of reflected waves R1 and R2, respectively. This difference may then be converted into a distance traveled by the reflected sound wave to get a thickness of the tar layer 186. Similarly, the thickness of the fiberglass layer 188 may be determined by causing one or more processors 42, 62 to calculate the difference in arrival times T2 and T3 and convert the calculated difference into a distance traveled by the reflected sound wave.

In another example, the transducer 165 of the 3D scanner 112 may transmit one or more ultrasonic sound waves and identify a frequency distribution of at least one received sound wave R1, R2, R3 and a frequency distribution of the at least one transmitted sound wave. As one of ordinary skill in the art will appreciate, the frequency distribution of a waveform may be identified by causing at least one processor 42, 62 to calculate the frequency distribution based on at least one recording of the waveform.

The one or more processors 42, 62 may also compare the frequency distribution of the at least one received sound wave R1, R2, R3 with the frequency distribution of the at least one transmitted sound wave and estimate a moisture level in one or more layers 184, 186, and 188. For example, the one or more processors 42, 62 may calculate a difference between the frequency distribution of the at least one received sound wave R1, R2, R3 and the frequency distribution of the at least one transmitted sound wave to determine if any moisture is present in one or more layers 184, 186, 188. The determined presence and/or level of moisture may then be used to estimate a condition of the structure 16.

More specifically, and in yet another example, a difference between the frequency distribution of the one or more transmitted sound waves and the one or more received sound waves R1, R2, R3 may be used to calculate a phase velocity of one or more of the received sound waves R1, R2, R3. This data can be used to indicate the moisture content within one of more of the shingle layer 184, the tar layer 186 or the fiberglass layer 188, for example. In another example, a difference between the frequency distribution of the one or more transmitted sound waves and the one or more received sound waves R1, R2, R3 may be used to calculate an attenuation within one or more of the shingle layer 184, the tar layer 186 or the fiberglass layer 188 that correspond to the one or more received sound waves R1, R2, R3. Changes in the calculated attenuation may indicate changes in moisture within one or more of the shingle, tar and fiberglass layers 184, 186, 188.

Figure 4C:
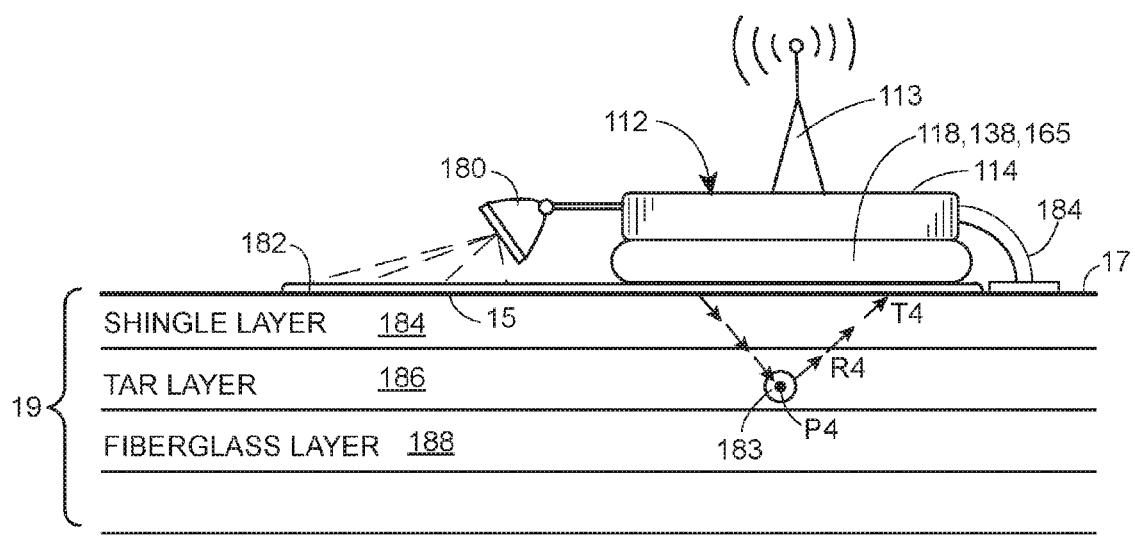
FIG. 4C is a cross-sectional view of the 3D scanner and the ultrasonic detection device of FIG. 4A, along with a subsurface of the structure, taken along the line A-A of FIG. 4A.

Referring now to FIG. 4C, another cross-section of subsurface 19 and a side view of the 3D scanner 112 along line A-A of FIG. 4A is depicted. As in FIG. 4B, the tar layer 186 includes another plurality of points 183, such as a fourth plurality of points 186 in the subsurface 19 of the structure 16, that includes another point P4. In certain examples, the plurality of points 183 may correspond to a defected or damaged area in at least one layer 184, 186, 188 of the subsurface 19, such as the tar layer 186. The defect or damage may include one or more of cracked shingles, damaged fiberglass mesh, moisture accumulation or structural weakness.

As further depicted in FIG. 4C, the 3D scanner 112 may identify, via one or more processors 62 of the ultrasonic detection device 138, for example, a time T4 corresponding to the reflected sound wave R4 received by the transducer 165. More specifically, the time T4 corresponds to the time from when the at least one sound wave is transmitted by the one or more transducers 165 to the at least one point P4 of the plurality of points 183 until the at least one reflected sound wave R4 is received by the at least one transducer 165. The received sound wave R4 may then be processed by the at least one processor 62 in the 3D scanner 112, such as the processor 42, and sent to the data analysis system 26 (FIG. 2). The data analysis system 26 may then identify, via one or more processors 52, at least one reflected sound wave R4 that corresponds to at least one defected or damaged area in at least one layer 184, 186, 188 of the subsurface 19.

In one example operation, the plurality of points 183 may correspond to a section of moisture in the tar layer 186. As the 3D scanner 112 passes over the section of moisture, the ultrasonic sound wave R4 may reflect off of a point P4 in the section of moisture and arrive back at the one or more transducers 165. The depth of the section of moisture may be determined by converting the time it took for the pulse to return into a distance. The particular layer that contains the plurality of points may also be identified. For example, if the 3D scanner 112 has already determined the thickness and number of layers in the area surrounding an identified defect or damaged area, the 3D scanner 112 may determine which layer contains the defect or damaged area by comparing the depth of the area with the known depth and thickness of the layers.

Figure 5A:
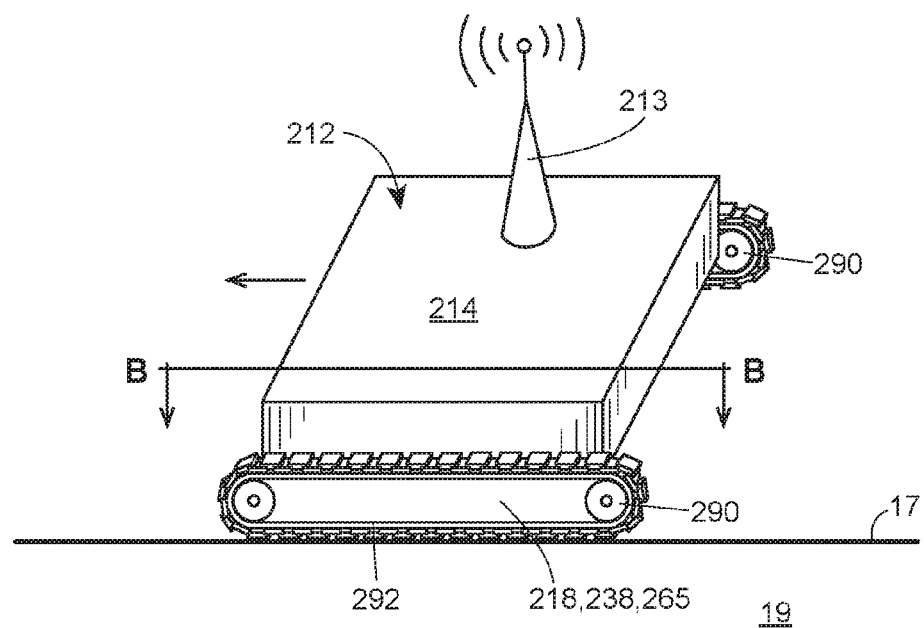
FIG. 5A is a perspective view of a 3D scanner and an ultrasonic detection device according to another aspect of the present disclosure.

Referring now to FIG. 5A, a 3D scanner 212 having an ultrasonic detection device 238 coupled thereto is depicted in contact with a top surface 17 of the structure 16 (FIG. 1). The 3D scanner includes a base 214, an antenna 213, a sensing system 218, the ultrasonic detection device 238, at least one transducer 265 and a continuous track system 290 coupled to the sides of the base 214 of the 3D scanner 212. The continuous track system 290 exists between the surface 17 of the structure 16 and the at least one transducer 265. The at least one transducer 265 slides over the continuous track system 290 as the continuous track system 290 stays stationary while underneath the 3D scanner 212. The continuous track system 290 may operate to propel the 3D scanner 212 along the surface 17 of the structure 16 and may also include a solid, sound conducting material. In this depiction, a substrate layer 292 sits between the at least one transducer 265 and the continuous track system 290. This substrate layer 292 may be a jelly-like sound conducting material and may also function as a lubricant between the at least one transducer 265 and the continuous track system 290. In addition, while depicted in FIG. 5A, the substrate layer 292 may not be required, and a continuous track system 290 that does not include the substrate layer 292 would still fall within the scope of the present disclosure.

In one example operation, as the 3D scanner 212 is moved across the top surface 17, the continuous track system 290 may rotate around the 3D scanner 212 such that, once the continuous track system 290 has come in contact with the surface 17, it will stay in contact with the same portion of the surface 17 until lifted off by the rotation. For example, as the 3D scanner 212 moves to the left as oriented in FIG. 5A, the continuous track system 290 would rotate counter clockwise relative to the 3D scanner 212. In this depiction, the continuous track system 290 is shown as two separate tracks on opposite sides of the 3D scanner 212. The continuous track system 290 may also surround the entire 3D scanner 212, or may only be in the middle of the 3D scanner 212 without departing from the scope of this disclosure. It is also not necessary that the continuous track system 290 itself propel the 3D scanner 212 over the surface 17 of the structure 16. As one of ordinary skill in the art will appreciate, the continuous track system 290 may also rotate passively as the 3D scanner 212 is propelled over the surface 17 by another system, such as wheels sitting under the base 214 or other propulsion systems. As one of ordinary skill in the art will further appreciate, the propulsion systems and/or types of locomotion may additionally or alternatively include a system having one or more of wheels, a snake, a walker, or a caterpillar and still fall within the scope of the present disclosure.

Figure 5B:
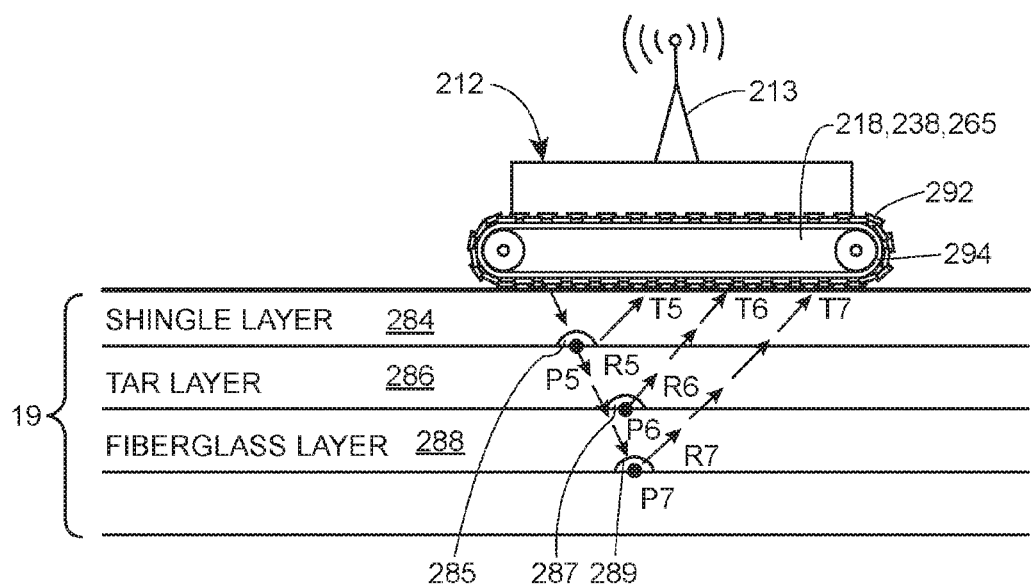
FIG. 5B is a cross-sectional view of the 3D scanner and the ultrasonic detection device of FIG. 5A, along with a subsurface of the structure, taken along the line B-B of FIG. 5A.

Referring now to FIG. 5B, a cross-section of subsurface 19 and a side view of the 3D scanner 212 along line B-B of FIG. 5A is depicted. The subsurface 19 includes a shingle layer 284, a tar layer 286 and a fiberglass layer 288, as well as other lower layers. Also depicted is a first plurality of points 285 disposed below the surface 17 of the structure or within the subsurface 19 of the structure 16. The plurality of points 285 includes at least one point P5 and corresponds to a region between the shingle layer 284 and the tar layer 286. The subsurface 19 further includes a second plurality of points 287, which includes at least one point P6 and corresponds to a region between the tar layer 286 and the fiberglass layer 288. The surface 19 still further includes a third plurality of points 289, which includes at least one point P7 and corresponds to a region between the fiberglass layer 288 and lower layers.

As further depicted in FIG. 5B, the at least one transducer 265 transmits at least one sound wave to the at least one point P5, P6, and/or P7 of one or more of the first, second, and third plurality of points 285, 287, 289 of the subsurface 19 of the structure 16. The at least one transducer 265 then receives one or more reflected sound waves R5, R6, and/or R7 from at least one point P5, P6, and/or P7 of the one or more of the first, second, and/or third plurality of points 285, 287, 289 of the subsurface 19 of the structure 16.

As further depicted in FIG. 5B, the 3D scanner 212 may identify, via one or more processors 62 of the ultrasonic detection device 238, for example, a time T5, T6, and/or T7 corresponding to at least one of the reflected sound waves R5, R6 and/or R7 received by the transducer 265. More specifically, the times T5, T6, and T7 correspond to times from when the at least one sound wave is transmitted by the one or more transducers 265 to the at least one point P5, P6, P7 of the plurality of points 285, 287, 289 until the at least one reflected sound wave R5, R6, R7 is received by the at least one transducer 265. The received sound waves R5, R6, R7 may then be processed by the at least one processor 62 in the 3D scanner 212, such as the processor 42, and sent to the data analysis system 26 (FIG. 2). The data analysis system 26 may then identify, via one or more processors 52, at least one reflected sound wave R5, R6 and/or R7 that corresponds to at least one layer 284, 286, 288 of the subsurface 19.

For example, the reflected wave R5 may correspond to a bottom of shingle layer 284 and the reflected waves R6 and R7 may correspond to a bottom of the tar layer 286 and fiberglass layer 288, respectively. As one of ordinary skill in the art will appreciate, several reflected sound waves are possible from the same transmitted wave, depending on the frequency of the sound wave and the acoustic characteristics of the layers of the subsurface 19. Also, reflected waves used by the 3D scanner 212 may come either from the same transmitted sound wave or separate transmitted sound waves. These separate sound waves may be calibrated to go deeper into the subsurface 19, for example, by adjusting the frequency to allow the ultrasound pulse to travel deeper into the subsurface 19 and into layers lower than the fiberglass layer 288.

In one example, when effecting a scan, the transducer 265 of the 3D scanner 212 may transmit one or more ultrasonic sound waves and measure the time it takes for at least a portion of the transmitted sound wave to reflect off of at least one point of a plurality of points that correspond to at least part of one or more layers of the subsurface 19. The 3D scanner 212 may then generate a plurality of 3D points based on the received one or more reflected sound waves.

The 3D scanner 212 may also calculate the number and thickness of the layers in subsurface 19. For example, the number of layers may be calculated by causing one or more processors 42, 62 to add up the total number of reflected sound waves received that correspond to one or more separate layers 284, 286, 288 of the subsurface 19. In another example, one or more processors 42, 62 may calculate a thickness of one or more of the layers 284, 286, 288 by converting the time between reflected sound waves that corresponds to one or more separate layers 284, 286, 288 of the subsurface 19 into distances traveled by the reflected sound waves using the speed of the sound waves in the medium. This distance may correspond to the thickness of one or more layers 284, 286, 288 of the subsurface 19.

In one example, to calculate the thickness of the tar layer 286, the 3D scanner 212 may send the data corresponding to reflected sound waves R5, R6 and R7 to the data analysis system 26. The data analysis system 26 may then cause one or more processors 42, 62 to calculate a difference in arrival times T5 and T6, of reflected waves R5 and R6, respectively. This difference may then be converted into a distance traveled by the reflected sound wave to get a thickness of the tar layer 286. Similarly, the thickness of the fiberglass layer 288 may be determined by causing one or more processors 42, 62 to calculate the difference in arrival times T6 and T7 and convert the calculated difference into a distance traveled by the reflected sound wave.

In another example, the transducer 265 of the 3D scanner 212 may transmit one or more ultrasonic sound waves and identify a frequency distribution of at least one received sound wave R5, R6, R7 and a frequency distribution of the at least one transmitted sound wave. As one of ordinary skill in the art will appreciate, the frequency distribution of a waveform may be identified by causing at least one processor 42, 62 to calculate the frequency distribution based on at least one recording of the waveform.

The one or more processors 42, 62 may also compare the frequency distribution of the at least one received sound wave R5, R6, R7 with the frequency distribution of the at least one transmitted sound wave and estimate a moisture level in one or more layers 284, 286, and 288. For example, the one or more processors 42, 62 may calculate a difference between the frequency distribution of the at least one received sound wave R5, R6, R7 and the frequency distribution of the at least one transmitted sound wave to determine if any moisture is present in one or more layers 284, 286, 288. The determined presence and/or level of moisture may then be used to estimate a condition of the structure 16.

More specifically, and in yet another example, a difference between the frequency distribution of the one or more transmitted sound waves and the one or more received sound waves R5, R6, R7 may be used to calculate a phase velocity of one or more of the received sound waves R5, R6, R7. This data can indicate the moisture content within the layer. In another example, a difference between the frequency distribution of the one or more transmitted sound waves and the one or more received sound waves R5, R6, R7 may be used to calculate an attenuation within the one or more shingle, tar or fiberglass layers 284, 286, 288 of the subsurface 19. Changes in the calculated attenuation may indicate changes in moisture within one or more of the shingle, tar, or fiberglass layers 284, 286, 288

Figure 5C:
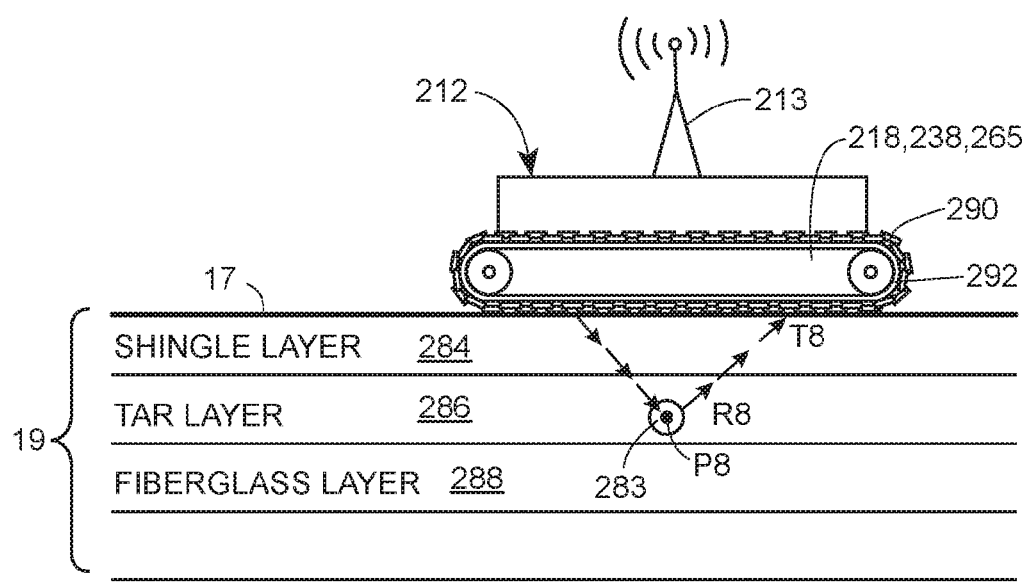
FIG. 5C is a cross-sectional view of the 3D scanner and the ultrasonic detection device of FIG. 5A, along with a subsurface of the structure, taken along the line B-B of FIG. 5A.

Referring now to FIG. 5C, another cross-section of subsurface 19 and a side view of the 3D scanner 212 along line B-B of FIG. 5A is depicted. In this example, the tar layer 286 includes another plurality of points 283 in the subsurface 19 of the structure 16 that includes another point P8. In certain examples, the plurality of points 283 may correspond to a defected or damaged area in at least one layer 284, 286, 288 of the subsurface 19, such as the tar layer 286. The defect or damage may include one or more of cracked shingles, damaged fiberglass mesh, moisture accumulation or structural weakness.

As further depicted in FIG. 5C, the 3D scanner 212 may identify, via one or more processors 62 of the ultrasonic detection device 238, for example, a time T8 corresponding to the reflected sound wave R8 received by the transducer 265. More specifically, the time T8 corresponds to the time from when the at least one sound wave is transmitted by the one or more transducers 265 to the at least one point P8 of the plurality of points 283 until the at least one reflected sound wave R8 is received by the at least one transducer 265. The received sound wave R8 may then be processed by the at least one processor 62 in the 3D scanner 212, such as the processor 42, and sent to the data analysis system 26 (FIG. 2), which may then identify, via one or more processors 42, at least one reflected sound wave R8 that corresponds to at least one defected or damaged area in at least one layer 284, 286, 288 of the subsurface 19.

In one example operation, the plurality of points 283 may correspond to a section of moisture in the tar layer 286. As the 3D scanner 212 passes over the section of moisture, the ultrasonic sound wave R8 may reflect off of a point P8 in the section of moisture and arrive back at the one or more transducers 265. The depth of the section of moisture may be determined by converting the time it took for the pulse to return into a distance. The particular layer that contains the plurality of points may also be identified. For example, if the 3D scanner 212 has already determined the thickness and number of layers in the area surrounding an identified defect or damaged area, the 3D scanner 212 may determine which layer contains the defect or damaged area by comparing the depth of the area with the known depth and thickness of the layers.

Figure 6A:
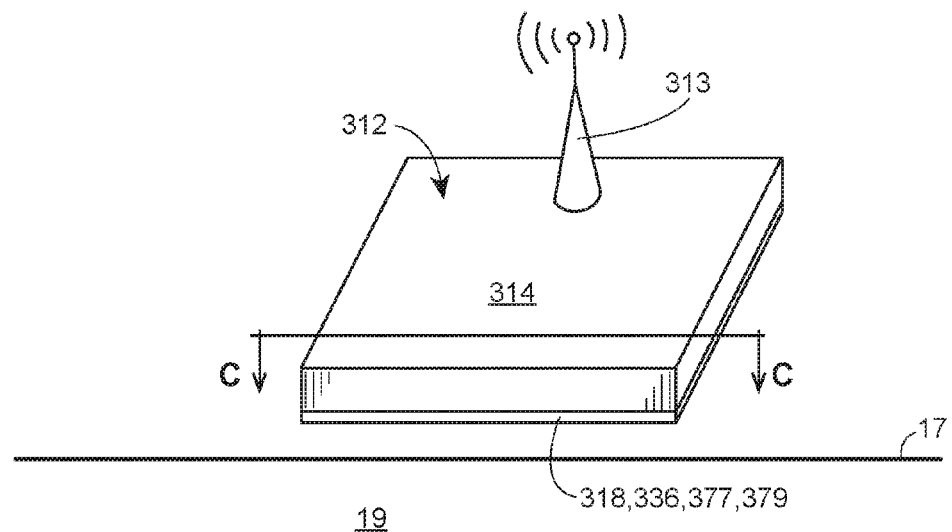
FIG. 6A is a perspective view of a 3D scanner and a radar sensing device according to another aspect of the present disclosure.

Referring now to FIG. 6A, a 3D scanner 312 having a radar sensing device 336 coupled thereto is depicted above a top surface 17 of the structure 16 (FIG. 1). The 3D scanner 312 includes a base 314, an antenna 313, a sensing system 318, the radar sensing device 336, at least one transmitter 377 and at least one receiver 379. As one of ordinary skill in the art will appreciate, the transmitter 377 and the receiver 379 may be configured to work with either electromagnetic energy pulses or ultrasonic sound waves and not depart from the scope of the present disclosure.

Figure 6B:
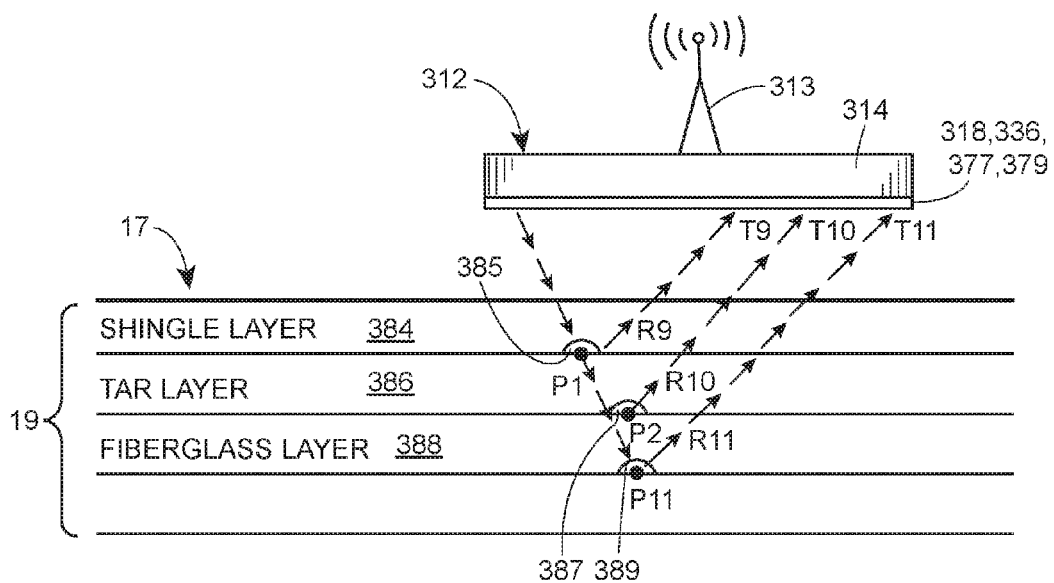
FIG. 6B is a cross-sectional view of the 3D scanner and the radar sensing device of FIG. 6A, along with a subsurface of the structure, taken along the line C-C of FIG. 6A.

Referring now to FIG. 6B, a cross-section of subsurface 19 and a side view of the 3D scanner 312 along line C-C of FIG. 6A is depicted. The subsurface 19 includes a shingle layer 384, a tar layer 386, and a fiberglass layer 388, as well as other lower layers. Also depicted is a first plurality of points 385 disposed below the surface 17 of the structure or within the subsurface 19 of the structure 16. The first plurality of points 385 includes at least one point P9 and corresponds to a region between the shingle layer 384 and the tar layer 386. The subsurface 19 further includes a second plurality of points 387, which includes at least one point P10 and corresponds to a region between the tar layer 386 and the fiberglass layer 388. The surface 19 still further includes a third plurality of points 389, which includes at least one point P11 and corresponds to a region between the fiberglass layer 388 and lower layers.

As further depicted in FIG. 6B, the at least one transmitter 377 and at least one receiver 379 (FIG. 3B) of the at least one radar sensing device 336 is positioned above the surface 17 of the structure 16. The at least one transmitter 377 then transmits at least one pulse to the at least one point P9, P10, and/or P11 of one or more of the first, second, and third plurality of points 385, 387, 389 of the subsurface 19 of the structure 16. The at least one receiver 379 then receives one or more reflected pulses R9, R10, and/or R11 from at least one point P9, P10, and/or P11 of the one or more of the first, second, and/or third plurality of points 385, 387, 389 of the subsurface 19 of the structure 16.

As further depicted in FIG. 6B, the 3D scanner 312 may identify, via one or more processors 72 of the radar sensing device 336, for example, a time T9, T10, and/or T11 corresponding to at least one of the reflected pulses R9, R10 and/or R11 received by the at least one receiver 379. More specifically, the times T9, T10, and T11 correspond to times from when the at least one pulse is transmitted by the one or more transmitters 377 to the at least one point P9, P10, P11 of the plurality of points 385, 387, 389 until the at least one reflected pulse R9, R10, R11 is received by the at least one receiver 379. The received pulses R9, R10, R11 may then be processed by the at least one processor 62 in the 3D scanner 312, such as the processor 42, and sent to the data analysis system 26 (FIG. 2). The data analysis system 26 may then identify, via one or more processors 52, at least one reflected pulses R9, R10 and/or R11 that correspond to at least one layer 384, 386, 388 of the subsurface 19.

For example, the reflected pulse R9 may correspond to a bottom of shingle layer 384 and the reflected pulses R10 and R11 may correspond to a bottom of the tar layer 386 and fiberglass layer 388, respectively. As one of ordinary skill in the art will appreciate, several reflected pulses are possible from the same transmitted pulse, depending on the frequency of the pulse and the characteristics of the layers of the subsurface 19. Also, reflected pulses used by the 3D scanner 312 may come from either the same transmitted pulse or separate transmitted pulses. These separate pulses may be calibrated to go deeper into the subsurface 19, for example, by adjusting the frequency to allow the pulse to travel deeper into the subsurface 19 and into layers lower than the fiberglass layer 388.

In one example, when effecting a scan, the transmitter 377 of the 3D scanner 312 may transmit one or more pulses and measure the time it takes for at least a portion of the transmitted pulse to reflect off of at least one point of a plurality of points that correspond to at least part of one or more layers of the subsurface 19. The 3D scanner 312 may then generate a plurality of 3D points based on the received one or more reflected pulses.

The 3D scanner 312 may also calculate the number and thickness of the layers in subsurface 19. In one example, the number of layers may be calculated by causing one or more processors 42, 72 to add up the total number of reflected pulses received that correspond to one or more separate layers 384, 386, 388 of the subsurface 19. In another example, one or more processors 42, 72 may calculate a thickness of one or more of the layers 384, 386, 388 by converting the time between reflected pulses that corresponds to one or more separate layers 384, 386, 388 of the subsurface 19 into distances traveled by the reflected pulses using the speed of the sound waves in the medium. This distance may correspond to the thickness of one or more layers 384, 386, 388 of the subsurface 19.

More specifically, to calculate the thickness of the tar layer 386, the 3D scanner 312 may send the data corresponding to reflected pulses R9, R10 and R11 to the data analysis system 26. The data analysis system 26 may then cause one or more processors 42, 72 to calculate a difference in arrival times T9 and T10 of reflected pulses R9 and R10, respectively. This difference may then be converted into a distance traveled by the reflected pulse to get a thickness of the tar layer 386. Similarly, the thickness of the fiberglass layer 388 may be determined by causing one or more processors 42, 72 to calculate the difference in arrival times T10 and T11 and convert the calculated difference into a distance traveled by the reflected pulse.

Figure 6C:
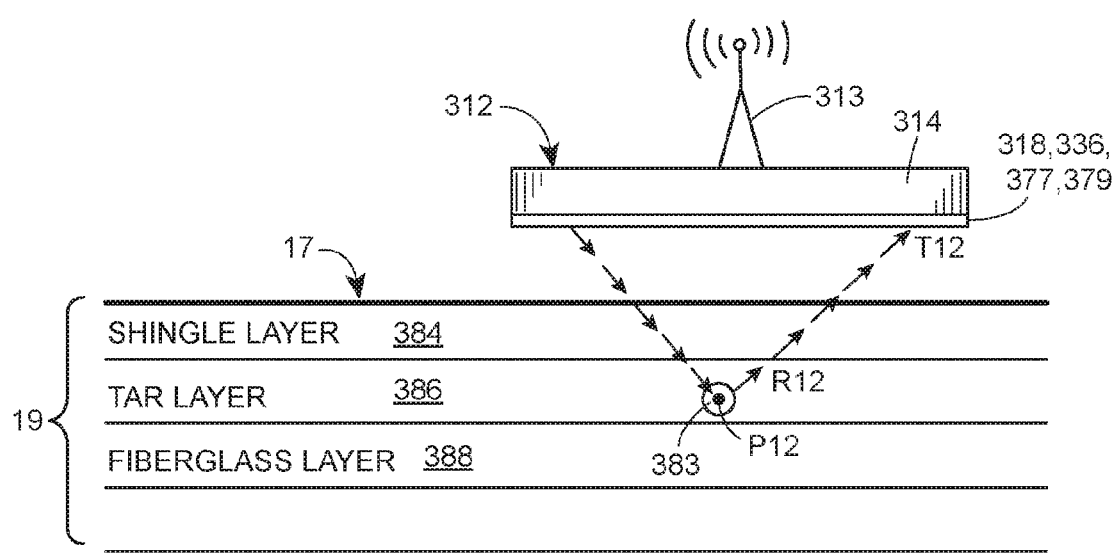
FIG. 6C is a cross-sectional view of the 3D scanner and the radar sensing device of FIG. 6A, along with a subsurface of the structure, taken along the line C-C of FIG. 6A.

Referring now to FIG. 6C, another cross-section of subsurface 19 and a side view of the 3D scanner 312 along line C-C of FIG. 6A is depicted. In this example, the tar layer 386 includes another plurality of points 383 that includes another point P12. In certain examples, the plurality of points 383 may correspond to a defected or damaged area in at least one layer 384, 386, 388 of the subsurface 19, such as the tar layer 386. The damage or defect may include one or more of cracked shingles, damaged fiberglass mesh, moisture accumulation or structural weakness.

As further depicted in FIG. 6C, the 3D scanner 312 may identify, via one or more processors 72 of the radar sensing device 336, for example, a time T12 corresponding to the reflected pulse R12 received by the at least one receiver 379. More specifically, the time T12 corresponds to the time from when the at least one pulse is transmitted by the one or more transmitters 377 to the at least one point P12 of the plurality of points 383 until the at least one reflected pulse R12 is received by the at least one receiver 379. The received pulse R12 may then be processed by the at least one processor 72 in the 3D scanner 312, such as the processor 42, and sent to the data analysis system 26 (FIG. 2). The data analysis system 26 may then identify, via one or more processors 52, at least one reflected pulse R12 that corresponds to at least one defected or damaged area in at least one layer 384, 386, 388 of the subsurface 19.

In one example operation, the plurality of points 383 may correspond to a section of moisture in the tar layer 386. As the 3D scanner 312 passes over the section of moisture, the radar pulse R12 may reflect off of a point P12 in the section of moisture and arrive back at the one or more receivers 379. The depth of the section of moisture may be determined by converting the time it took for the pulse to return into a distance. The particular layer that contains the plurality of points may also be identified. For example, if the 3D scanner 312 has already determined the thickness and number of layers in the area surrounding an identified defect or damaged area, the 3D scanner 312 may determine which layer contains the defect or damaged area by comparing the depth of the area with the known depth and thickness of the layers.

Figure 7:
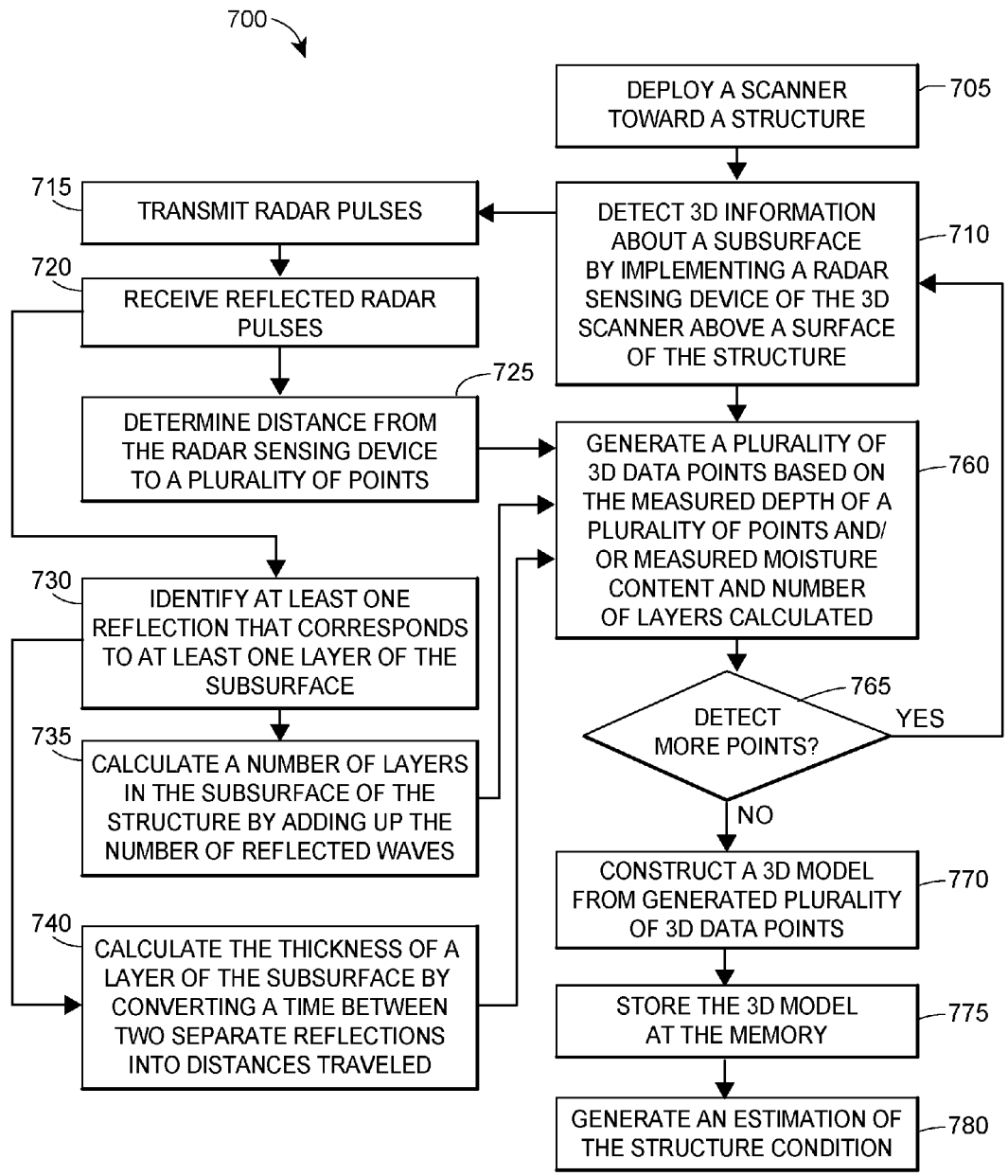
FIG. 7 is an exemplary flow chart depicting a method of one aspect of the present disclosure.

Referring now to FIG. 7, a flowchart of an example method 700 for inspecting the condition of the subsurface of a structure using a radar sensing device is depicted. The method 700 may be implemented, in whole or in part, on one or more devices or systems such as those shown in the property inspection system 10 of FIGS. 1 and 2, the radar sensing device 36 of FIG. 3B, or the 3D scanner 312 and radar sensing device 336 of FIG. 6A. The method may be saved as a set of instructions, routines, programs, or modules on memory such as memory 44 of FIG. 2, and may be executed by a processor such as processor 42 of FIG. 2.

The method 700 begins when a 3D scanner 12, 312 is deployed toward a structure, such as the structure 16 shown in FIG. 1. After deployment, the 3D scanner 12, 312 detects 3D information about the subsurface by implementing the radar sensing device 36, 336 of the 3D scanner 12, 312 above the surface 17 of the structure 16 (block 710). Said another way, the 3D scanner 12, 312 detects a point of the plurality of points 383, 385, 387, 389 (FIGS. 6B and 6C), for example, in the subsurface 19 (FIG. 6A) of the structure 16 by having the radar sensing device 36, 336 scan the subsurface 19 from above the surface 17 of the structure 16. As noted, the structure 16 may be any kind of building or structure, such as a single-family home, townhome, condominium, apartment, storefront, or retail space, and the structure 16 may be owned, leased, possessed, or occupied by an insurance policy holder. The structure 16 may also be any of the structure types discussed regarding FIG. 1, such as a vehicle, boat, or aircraft. In such structures, the 3D contact scanner 12, 312 may be used to inspect the body panels, windows, frame and other surfaces associated with the vehicle, boat, or aircraft.

In block 715, the transmitter 77, 377 of the radar sensing device 36, 336 transmits at least one radar pulse towards the surface 17 of the structure 16. As one of ordinary skill in the art will appreciate, the radar pulses may consist of either electromagnetic energy pulses or sound waves and not depart from the scope of the present disclosure. In block 720, the receiver 79, 379 of the radar sensing device 36, 336 receives at least one radar pulse after reflecting off of at least one point P9, P10, P11, P12 of a plurality of points 383, 385, 387, 389 in the subsurface 19. In block 725, the 3D scanner 12, 312 may then determine the distance from the radar sensing device 36, 336 to the one or more plurality of points 383, 385, 387, 389 that the at least one radar pulse reflected off. This may be done by converting the time from transmitting the radar pulse to receiving the reflected radar pulse into a distance traveled. In block 760, the 3D scanner 12, 312 then generates a plurality of 3D data points based on the measured depth of a plurality of points.

In addition or alternatively, after block 720, the reflected radar pulses are identified that correspond to at least one layer of the structure are identified at block 730. In block 735, the number of layers in the subsurface 19 can be calculated by adding up the number of reflected radar pulses that correspond to individual layers of the subsurface 19. The calculated number of layers may then be used in block 760 to generate a plurality of 3D data points. In addition or alternatively, after block 730, the thickness of at least one layer may be calculated by converting a time between at least two separate reflected radar pulses corresponding to at least two separate layers of the subsurface 19 into distances traveled by the radar pulses. The calculated thickness of at least one layer may then be used in block 760 to generate a plurality of 3D data points.

At block 765, at least one processor, such as the processor 42 of the 3D scanner 12, 312 determines whether enough points of the plurality of points 383, 385, 387, 389 of the subsurface 19 of the structure 16 have been detected or whether more points need to be detected. If enough points have been detected, a processor 42 of the 3D scanner 12, 312 constructs a 3D model from the generated plurality of 3D data points (block 770). Next the processor 42 of the 3D scanner 12, 312 may cause the 3D model to be stored at the memory 54 of the data analysis system 26 of the property inspection system 10 (block 775). At block 780, the processor 42, for example, communicatively connected to a memory 44 of the 3D scanner 12, 213 or the memory 54 of the data analysis system 26 generates an estimate or an estimation of the condition of the subsurface 19 of the structure 16 based on the plurality of 3D data points.

If, however, at block 765, it is determined that more points need to be detected, the 3D scanner 12, 312 detects more 3D information by implementing the radar sensing device 36, 336 of the 3D scanner 12, 312 again above the surface 17 of the structure 16 (block 710). Then once again, the 3D scanner 12, 312 with the radar sensing device 36, 336 transmits at least one radar pulse toward the surface 17 of the structure 16 (block 715). The process of blocks 715, 720, 725, 730, 735, 740 and/or 760 will continue until it is determined at block 765 that enough points have been detected. The process of blocks 770, 775, and 780, as described above, then continue to ultimately construct a 3D model from the generated plurality of 3D data points, store that model at the memory 54 of the data analysis system 26, for example, and generate an estimate of the condition of the subsurface 19 of the structure 16 based on the plurality of 3D data points, respectively.

Figure 8:
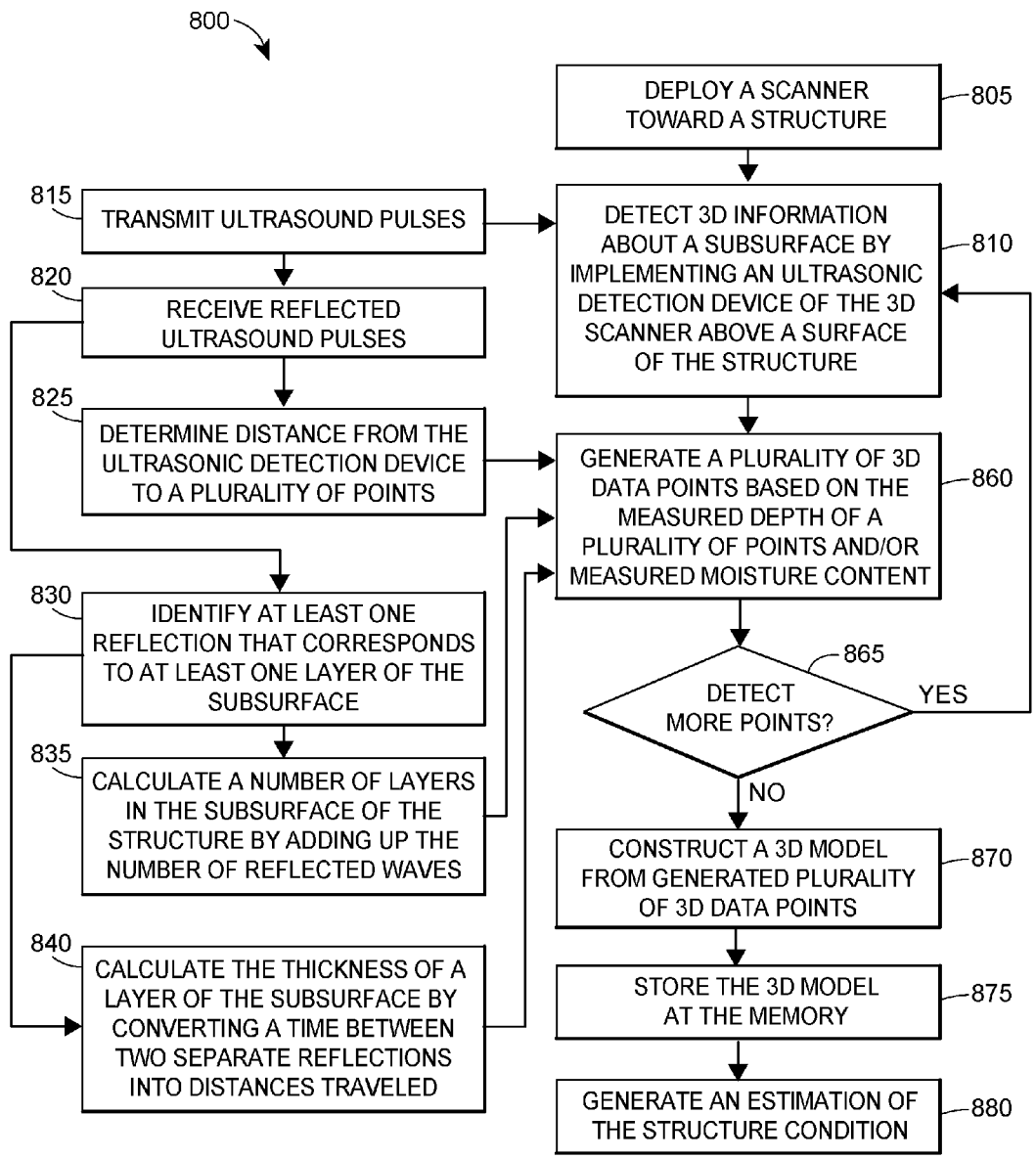
FIG. 8 is another exemplary flow chart depicting a method of another aspect of the present disclosure.

Referring now to FIG. 8, a flowchart of an example method 800 for inspecting the condition of the subsurface of a structure using an ultrasound detection device is depicted. The method 800 may be implemented, in whole or in part, on one or more devices or systems such as those shown in the property inspection system 10 of FIGS. 1 and 2, the ultrasonic detection device 38 of FIG. 3A, or the 3D scanner 112, 212 and ultrasonic detection device 138, 238 of FIGS. 4A and 5A. The method may be saved as a set of instructions, routines, programs, or modules on memory such as memory 44 of FIG. 2, and may be executed by a processor such as processor 42 of FIG. 2.

The method 800 begins when a 3D scanner 12, 112, 212 is deployed toward a structure, such as the structure 16 shown in FIG. 1. After deployment, the 3D scanner 12, 112, 212 detects 3D information about the subsurface by implementing an ultrasonic detection device 38, 138, 238 of the 3D scanner 12, 112, 212 above the surface 17 of the structure 16 (block 810). Said another way, the 3D scanner 12, 112, 212 detects a point of the plurality of points 183, 185, 187, 189, 283, 285, 287, 289 (FIGS. 1 and 2), for example, in the subsurface 19 (FIGS. 4A and 5A) of the structure 16 by having the ultrasonic detection device 38, 138, 238 scan the subsurface 19 from above the surface 17 of the structure 16.

In block 815, the transducer 65, 165, 265 of the ultrasound detection device 38, 138, 238 transmits at least one pulse, e.g., such as a sound wave, towards the surface 17 of the structure 16. In block 820, the transducer 65, 165, 265 of the ultrasonic sensing device 38, 138, 238 receives at least one sound wave after reflecting off of at least one point P1, P2, P3, P4, P5, P6, P7, P8 of a plurality of points 183, 185, 187, 189, 283, 285, 287, 289 in the subsurface 19. In block 825, the 3D scanner 12, 112, 212 may then determine the distance from the ultrasonic sensing device 38, 138, 238 to the plurality of points that the at least one sound wave reflected off. This may be done by converting the time from transmitting the radar pulse to receiving the reflected sound wave into a distance traveled. In block 860, the 3D scanner 12, 112, 212 then generates a plurality of 3D data points based on the measured depth of a plurality of points.

In addition or alternatively, after block 820, the reflected sound waves that correspond to at least one layer of the structure 16 may be identified at block 830. In block 835, the number of layers in the subsurface 19 can be calculated by adding up the number of reflected sound waves that correspond to individual layers of the subsurface 19. The calculated number of layers may then be used in block 860 to generate a plurality of 3D data points. In addition or alternatively, after block 830, the thickness of at least one layer may be calculated by converting a time between at least two separate reflected sound waves corresponding to at least two separate layers of the subsurface 19 into distances traveled by the sound waves. The calculated thickness of at least one layer may then be used in block 860 to generate a plurality of 3D data points.

At block 865, at least one processor, such as the processor 42 of the 3D scanner 12, 112, 212 determines whether enough points of the plurality of points 183, 185, 187, 189, 283, 285, 287, 289 of the subsurface 19 of the structure 16 have been detected or whether more points need to be detected. If enough points have been detected, a processor 42 of the 3D scanner 12, 112, 212 constructs a 3D model from the generated plurality of 3D data points (block 870). Next the processor 42 of the 3D scanner 12, 112, 212 may cause the 3D model to be stored at the memory 54 of the data analysis system 26 of the property inspection system 10 (block 875). At block 880, the processor 42, for example, communicatively connected to a memory 44 of the 3D scanner 12, 112, 212 or the memory 54 of the data analysis system 26 generates an estimate or an estimation of the condition of the subsurface 19 of the structure 16 based on the plurality of 3D data points.

If, however, at block 865, it is determined that more points need to be detected, the 3D scanner 12, 112, 212 detects more 3D information by implementing the ultrasound detection device 38, 138, 238 of the 3D scanner 12, 112, 212 again above the surface 17 of the structure 16 (block 810). Then once again, the 3D scanner 12, 112, 212 with the ultrasound detection device 38, 138, 238 transmits at least one sound wave toward the surface 17 of the structure 16 (block 815). The process of blocks 815, 820, 825, 830, 835, 840 and/or 860 will continue until it is determined at block 865 that enough points have been detected. The process of blocks 870, 875, and 880, as described above, then continue to ultimately construct a 3D model from the generated plurality of 3D data points, store that model at the memory 54 of the data analysis system 26, for example, and generate an estimate of the condition of the subsurface 19 of the structure 16 based on the plurality of 3D data points, respectively.

While the layers of the subsurface 19 depicted in FIGS. 4B, 4C, 5B, 5C, 6B and 6C include a shingle layer 184, 284, 384, a tar layer 186, 286, 386, and a fiberglass layer 188, 288, 388, one of ordinary skill in the art will understand that one or more of the shingle layer 184, 284, 384, the tar layer 186, 286, 386, and the fiberglass layer 188, 288, 388 may include one or more various materials, including, but not limited to, plastics, composites, ceramic, and/or metal. In addition, or alternatively, the subsurface 19 of the structure 16 may include other layers between, above and/or further beneath one or more of the shingle layer 184, 284, 384, the tar layer 186, 286, 386, and the fiberglass layer 188, 288, 388, such as a layer or an area having one or more of plastics, composites, ceramic or metal, for example, and still fall within the scope of the present disclosure. Further, while the shingle layer 184, 284, 384 may include a typical asphalt shingle layer and its well-known materials and properties, one of ordinary skill in the art will further understand that a roof may include one or more of plastic, ceramic or metal shingles or surfaces and still fall within the scope of the present disclosure.

Overall, one of ordinary skill in the art will appreciate the various advantages of the property inspection system 10 of the present disclosure. For example, the property inspection system 10 of the present disclosure is able to accurately detect 3D information about the subsurface of a structure using one or more of the ultrasonic detection device 38, 138, 238 or the radar sensing device 36, 336. By using radar pulses of the radar sensing device 36, 336, for example, to detect 3D information about the subsurface of the structure, any interfering sunlight or lack thereof does not affect the accuracy of the information being detected, and significantly greater detail about subsurface layers is accurately detected. In addition, while the ultrasonic detection devices 38, 138 may apply a substrate to a surface of the structure before and/or during a scan, such devices 12, 112 further remove excess substrate from the surface of the structure during or after a scan is complete via the suction device 184. In another example, a substrate is not directly applied to the surface 17 of the structure 16; instead, a substrate layer 292 is disposed within the continuous track system coupled 290 to the 3D scanner 212, such that the substrate layer 292 surrounds at least part of the ultrasonic detection device 238. As a result, removal of any substrate sprayed onto the surface 17 of the structure 16 is not required in this example. For at least these reasons, the process and system 10 of the present disclosure using the ultrasonic detection devices 38, 138, 238 includes significantly less, if any, substrate removal after the 3D scanner 12, 112, 212, 312 completes a scan, reducing the mess, time and cost associated with the 3D scanning process.

Still further, and unlike other 2D and 3D scanning methods, both the ultrasonic detection devices 38, 138, 238 and the radar sensing device 36, 336 of the property inspection systems and methods of the present disclosure are able to detect damage and defects to subsurface layers of the structure not apparent on the top surface of the structure. For example, 3D scanning methods using tactile sensors are unable to detect damage to the subsurface of the structure when the surface of the structure appears free of any defect. The systems and methods of the present disclosure, however, are able to detect specific points of damage at and/or with several layers of the subsurface of the structure below the surface of the structure, providing significantly more accurate detail and information about a condition of the structure. As a result, the accuracy of damage estimates is greatly improved.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Discussions herein referring to an "appraiser," "inspector," "adjuster," "claim representative" or the like are non-limiting. One skilled in the art will appreciate that any user associated with an insurance company or an insurance function may utilize one or more of the devices, systems, and methods disclosed in the foregoing description. One skilled in the art will further realize that any reference to a specific job title or role does not limit the disclosed devices, systems, or methods, or the type of user of said devices, systems, or methods.

Certain implementations are described herein as including logic or a number of components, modules, or mechanisms. Modules may constitute either software modules (e.g., code implemented on a tangible, non-transitory machine-readable medium such as RAM, ROM, flash memory of a computer, hard disk drive, optical disk drive, tape drive, etc.) or hardware modules (e.g., an integrated circuit, an application-specific integrated circuit (ASIC), a field programmable logic array (FPLA)/field-programmable gate array (FPGA), etc.). A hardware module is a tangible unit capable of performing certain operations and may be configured or arranged in a certain manner. In example implementations, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one implementation," "one embodiment," "an implementation," or "an embodiment" means that a particular element, feature, structure, or characteristic described in connection with the implementation is included in at least one implementation. The appearances of the phrase "in one implementation" or "in one embodiment" in various places in the specification are not necessarily all referring to the same implementation.

Some implementations may be described using the expression "coupled" along with its derivatives. For example, some implementations may be described using the term "coupled" to indicate that two or more elements are in direct physical or electrical contact. The term "coupled," however, may also mean that two or more elements are not in direct contact with each other, but yet still co-operate or interact with each other. The implementations are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the implementations herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for inspecting a structure to estimate the condition of a structure through the disclosed principles herein. Thus, while particular implementations and applications have been illustrated and described, it is to be understood that the disclosed implementations are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

We claim:

1. A method of inspecting a structure, the method comprising:
   deploying one or more three-dimensional (3D) scanners to scan a structure, wherein the one or more 3D scanners are communicatively coupled to a memory;
   detecting 3D information about a subsurface of the structure by implementing a sensing device including one or more of a radar sensing device or an ultrasonic detection device coupled to the one or more 3D scanners, wherein implementing the sensing device includes:
   transmitting, via at least one transmitter, pulses to at least one point of a plurality of points of the subsurface of the structure;
   receiving, via at least one receiver, one or more reflected signals from at least one point of a plurality of points of the subsurface of the structure; and
   determining, via one or more processors, a distance from one of the radar sensing device or the ultrasonic detection device to at least one point of the plurality of points of the subsurface of the structure based on the at least one received reflected signal;
   generating, at the one or more 3D scanners, a plurality of 3D data points, wherein at least one point of the plurality of 3D data points corresponds to at least one point of a plurality of points in the subsurface of the structure detected by the radar sensor device or the ultrasonic detection device during the scan of the structure; and
   causing a processor communicatively connected to the memory to generate an estimation of the condition of the subsurface of the structure based on the plurality of 3D data points,
   wherein receiving, via the at least one receiver, one or more reflected signals from at least one point of a plurality of points of the subsurface of the structure includes: receiving one or more waves, via at least one receiver, reflected off of at least part of the subsurface of the structure, and
   identifying, via one or more processors, at least one reflection that corresponds to at least one layer of the subsurface of the structure, the at least one layer including one of a shingle layer, a tar layer, a fiberglass mesh layer or a lower layer disposed beneath the fiberglass mesh layer of a roof of the structure.

2. The method of claim 1, further comprising causing a processor communicatively coupled to the memory to construct a 3D model from the generated plurality of 3D data points and analyze the 3D model to identify one or more features associated with the structure.

3. The method of claim 1, wherein the sensing device comprises the radar sensing device, and deploying one or more 3D scanners includes positioning the radar sensing device coupled to the one or more 3D scanners at an elevation higher than at least part of a surface of the structure.

4. The method of claim 1, wherein receiving, via the at least one receiver, one or more reflected signals from at least one point of a plurality of points of the subsurface of the structure includes: receiving one or more waves, via at least one receiver, reflected off of at least part of the subsurface of the structure.

5. The method of claim 4, wherein generating, at one or more 3D scanners, the plurality of 3D points comprises:
   identifying a first reflection of the one or more waves off of at least part of the subsurface or surface of the structure at the radar sensing device or the ultrasonic detection device at a first time;
   identifying a second reflection of the one or more waves off of at least part of the subsurface or surface of the structure at one or more of the radar sensing device or the ultrasonic detection device at a second time different from the first time; and
   identifying a third reflection of the one or more waves off of at least part of the subsurface of surface of the structure at one or more of the radar sensing device or the ultrasonic device at a third time different from the first and second times.

6. The method of claim 5, further including recording at least the first, second, and third times, via one or more processors, of the first, second, and third reflections of the one or more waves off of at least one point of a plurality of points of the subsurface or surface of the structure.

7. The method of claim 1, further comprising calculating, via one or more processors, a number of layers in the subsurface of the structure by adding up a number of reflections received by the at least one receiver that corresponds to one or more separate layers of the subsurface.

8. The method of claim 4, further comprising calculating, via one or more processors, a thickness of at least one layer of the subsurface by converting a time between at least two separate reflections into distances traveled by the waves, the distance corresponding to at least one layer of the structure.

9. The method of claim 1, wherein
detecting 3D information about a subsurface of the structure by implementing the ultrasonic detection device coupled to the one or more 3D scanners across a surface of the structure further includes applying a sound conducting material to the plurality of points on a surface of the structure; and
positioning at least one transducer of at least one ultrasonic detection device onto a portion of the substrate applied to the surface of the structure, such that the at least one transducer physically contacts the sound conducting material that is in contact with the surface of the structure before transmitting pulses to at least one point of the plurality of points of the subsurface of the structure.

10. The method of claim 9, further comprising collecting remaining sound conducting material disposed on the surface of the structure via one or more of a suction device or vacuum coupled to the 3D scanner.

11. The method of claim 1, further comprising identifying, via one or more processors, a first plurality of points within a shingle layer of the subsurface, a second plurality of points within a tar layer of the subsurface, and a third plurality of points within a fiberglass layer of the subsurface.

12. A property inspection system for inspecting the condition of a physical structure, the property inspection system comprising:
one or more three-dimensional (3D) scanners adapted to scan a surface of the roof;
a sensing device including one or more of a radar sensing device or an ultrasonic detection device coupled to the one or more 3D scanners, each of the radar sensing device and the ultrasonic detection device having at least one transmitter, at least one receiver, and at least one processor, each sensing device adapted to detect 3D information about a subsurface of the structure by: (1) transmitting, via the at least one transmitter, pulses to at least one point of a plurality of points of the subsurface of the structure; (2) receiving, via at least one receiver, one or more reflected pulses from at least one point of a plurality of points of the subsurface of the structure, including receiving one or more waves, reflected off of at least part of the subsurface of the structure, and identifying, via one or more processors, at least one reflection that corresponds to at least one layer of the subsurface of the structure, the at least one layer including one of a shingle layer, a tar layer, a fiberglass mesh layer or a lower layer disposed beneath the fiberglass mesh layer of the roof of the structure; and (3) determining, via at least one processor, a distance from one or more of the devices to at least one point of the plurality of points of the subsurface of the structure based on the at least one received reflected pulse;
at least one processor adapted to generate 3D data points corresponding to the 3D information detected by the radar sensing device or the ultrasonic sensing device;
a memory, communicably coupled to the one or more 3D scanners, adapted to store 3D data points generated by the one or more processors and the 3D information detected by the radar sensing device or the ultrasonic sensing device; and
a network interface, communicably coupled to the one or more processors, adapted to transmit the 3D data points to a data analysis system for estimating the condition of the subsurface of the structure.

13. The system of claim 12, wherein the at least one processor is further adapted to generate a 3D model based, at least in part, on the generated 3D data points of the 3D information detected by one or more of the radar sensing device and the ultrasonic detection device, and the memory is further adapted to store the 3D model.

14. The system of claim 12, wherein at least one of the one or more 3D scanners is physically connected to a flying device.

15. The system of claim 12, wherein the sensing device is the ultrasonic detection device, and the ultrasonic detection device further includes a body having at least one transducer including the at least one transmitter and the at least one receiver, and the 3D scanner includes a base and a spraying mechanism coupled to the base, the spraying mechanism adapted to apply a substrate to a plurality of points on the surface of the structure.

16. The system of claim 15, further including a suction device that is coupled to the base, the suction device adapted to collect the substrate from a plurality of points on the surface of the structure after or during the scan.

* * * * *